United States Patent [19]

Wommack

[11] 4,061,788
[45] Dec. 6, 1977

[54] WORM DETECTION PROCESS

[76] Inventor: Malcolm R. Wommack, 603 N. Pearl, Comanche, Tex. 76442

[21] Appl. No.: 640,586

[22] Filed: Dec. 15, 1975

[51] Int. Cl.$^2$ ............................................. A23L 3/28
[52] U.S. Cl. .................................. 426/248; 426/93; 426/251; 426/479; 426/629; 99/451
[58] Field of Search .................. 426/237, 93, 302, 309, 426/248, 251, 479, 629, 632, 231; 250/302; 209/3, 111.5

[56] References Cited

U.S. PATENT DOCUMENTS

| | | | |
|---|---|---|---|
| 2,451,528 | 10/1948 | Armstrong | 209/3 |
| 3,057,733 | 10/1962 | Frost | 426/251 |
| 3,305,089 | 2/1967 | Fraenkel | 209/111.5 |
| 3,418,078 | 12/1968 | Mlot-Fivalkowski | 250/302 |
| 3,477,858 | 11/1969 | Wells et al. | 426/251 |
| 3,506,827 | 4/1970 | Alburger | 250/302 |
| 3,530,295 | 9/1970 | Alburger | 250/302 |

OTHER PUBLICATIONS

Gecan et al., J. of Food Science, vol. 36 (1971), pp. 89-92.
Gecan et al., J. Ass. Office. Anal. Chem., 53(3): 550-551 (1970).

Primary Examiner—Raymond N. Jones
Assistant Examiner—C. A. Fan
Attorney, Agent, or Firm—Wofford, Felsman, Fails & Zobal

[57] ABSTRACT

A process for enhancing the detection of larvae or worms in shelled pecans for separation and removal therefrom. In carrying out the process, the shelled pecans are soaked in a solution comprising a water soluble, edible, non-fluorescent material dissolved in water to coat the pecans with the material. The pecans are removed from the solution, dried, and illuminated with ultraviolet light. The material does not adhere to the worms whereby it does not affect their fluorescence but prevents the pecans from fluorescing whereby the worms may be readily detected and separated. The color of the material used is such that it does not significantly affect the appearance of the pecans when coated therewith.

16 Claims, 5 Drawing Figures

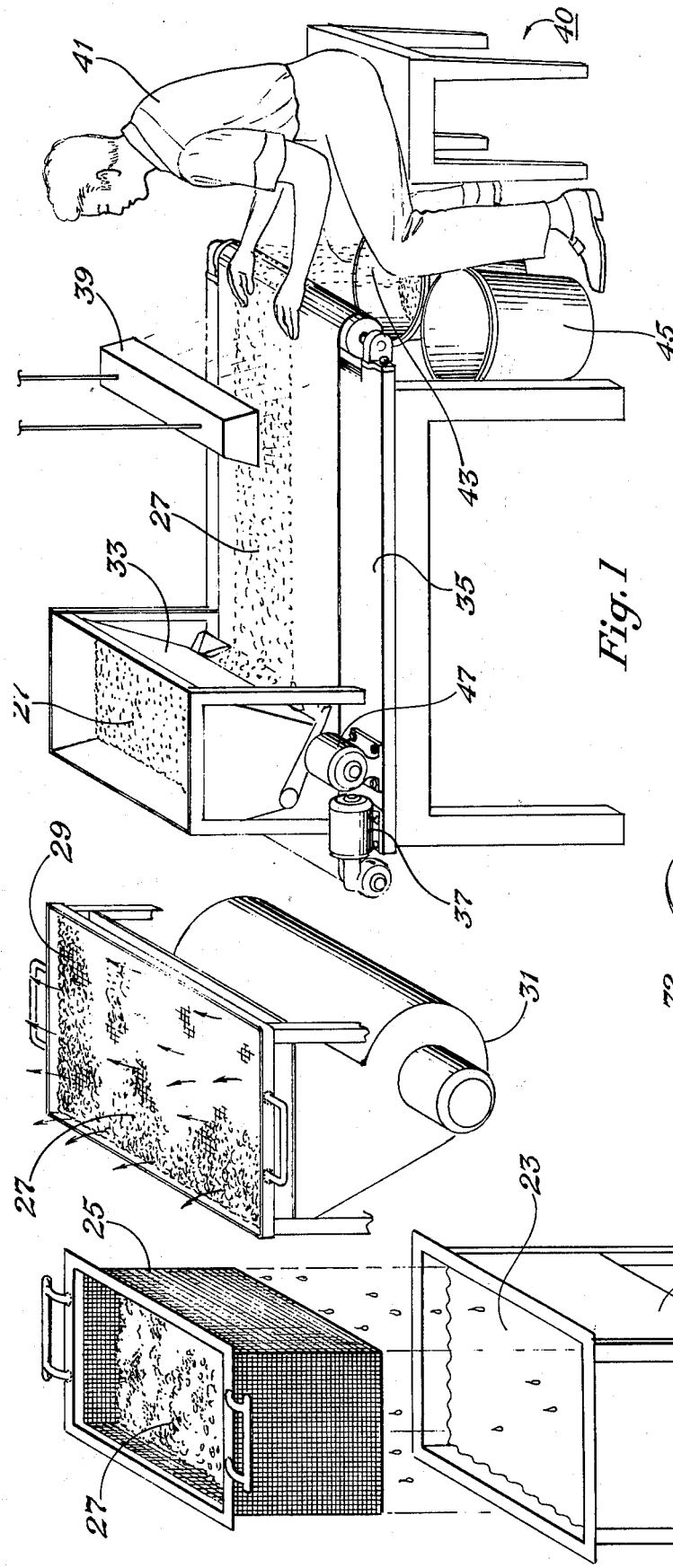
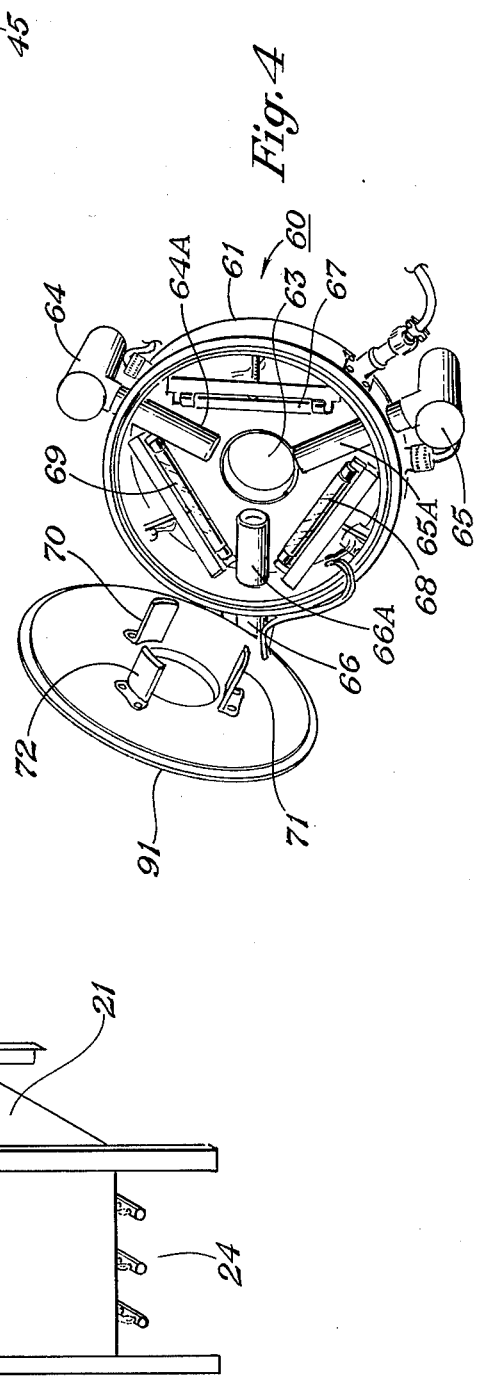

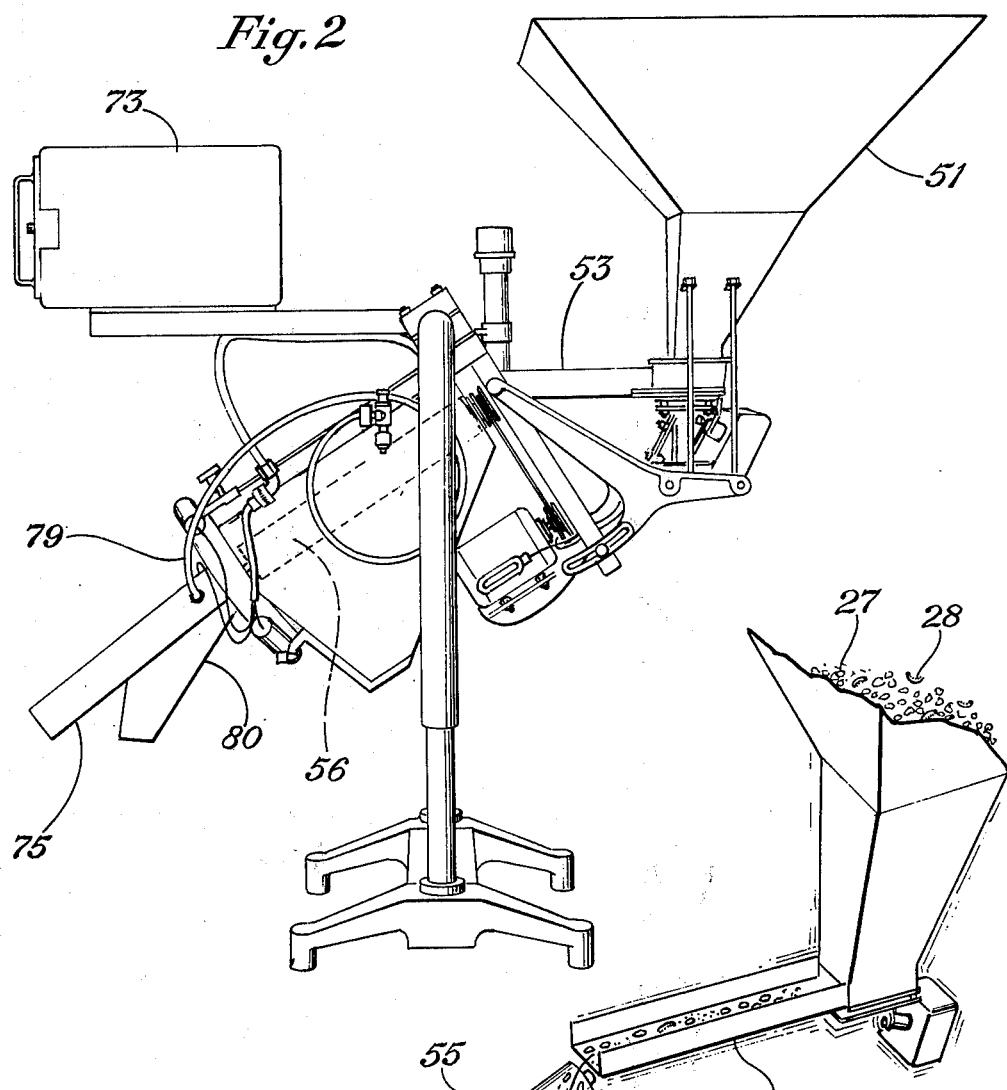
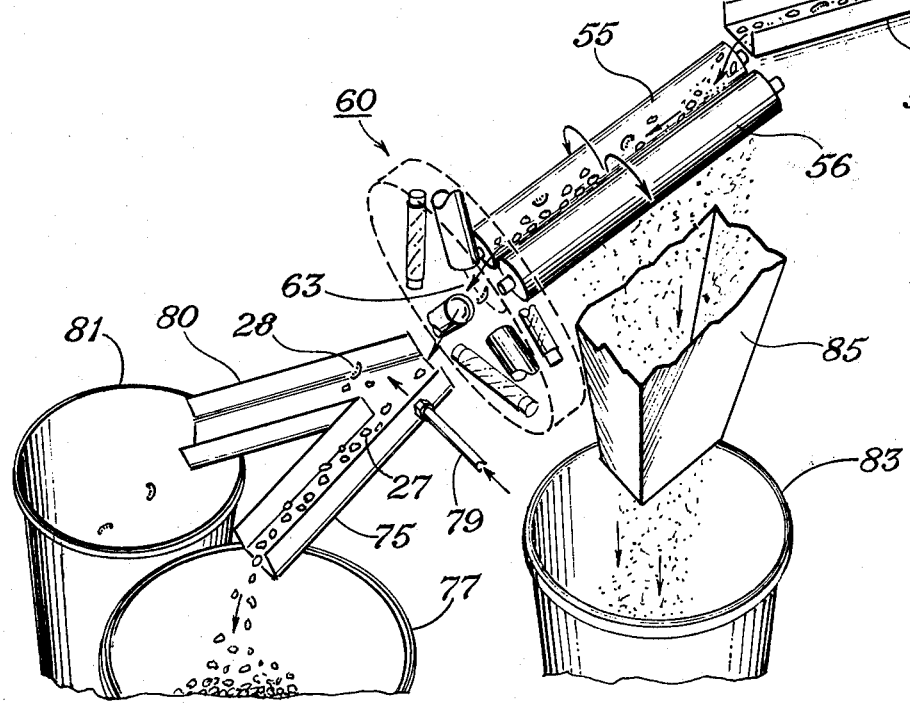

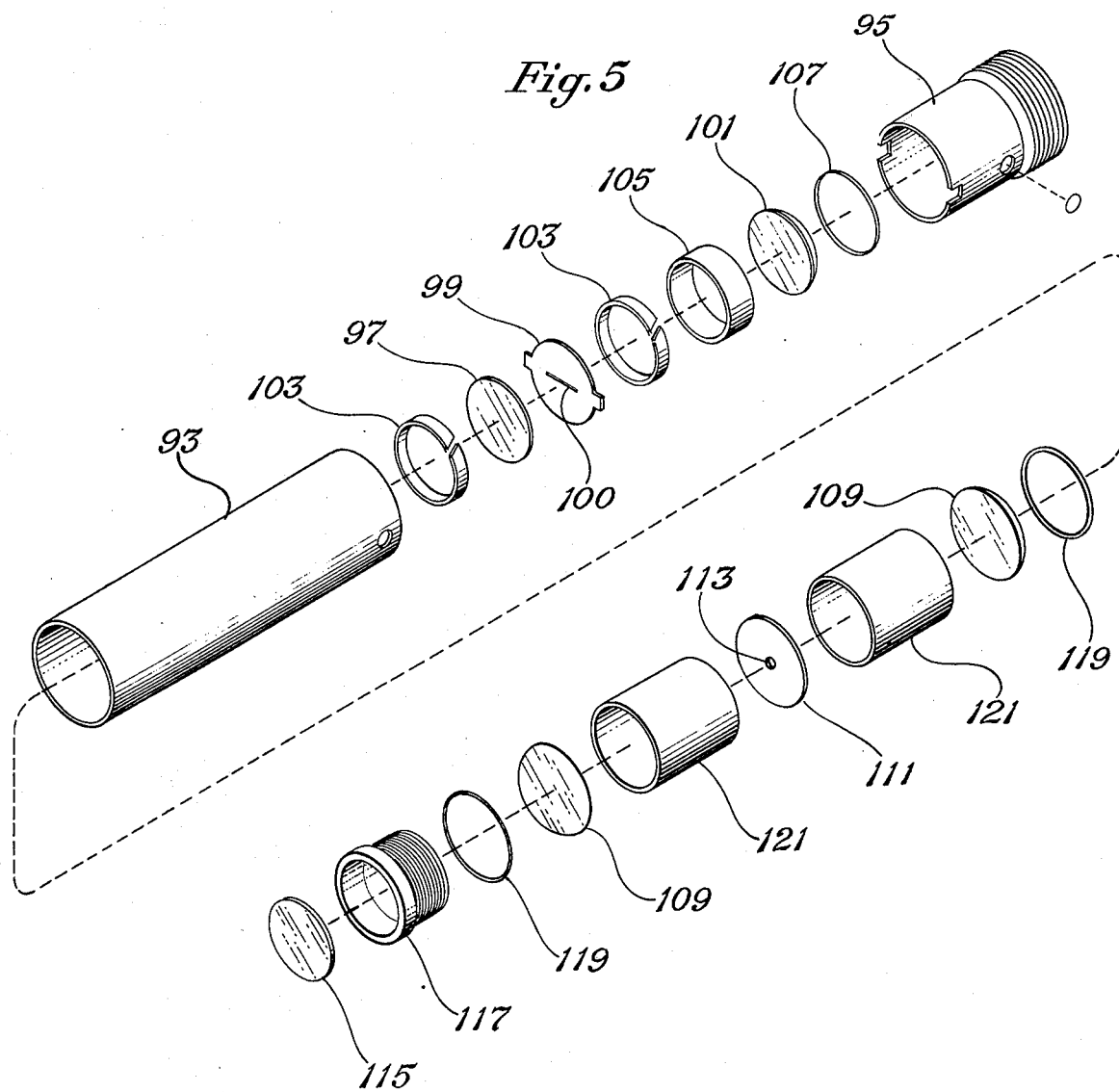

WORM DETECTION PROCESS

BACKGROUND OF THE INVENTION:

This invention relates to a process and system for enhancing the detection of larvae or worms in shelled nuts for separation and removal therefrom.

The pecan weevil Curculio Caryae, is a late-season pest of pecans. The weevil appears in late August and early September. After the nut kernals begin to form, the female chews a hole in the shell and deposits her eggs in little pockets in the nuts. Creamy, worm-like larvae or grubs hatch from the eggs and feed inside the nuts during the fall. When they reach maturity, the grubs chew a hole in the shell, emerge from the nut and drop to the ground in late fall and early winter. They burrow in the soil and transfer to pupae. The adults appear during the summer, following pupation and the cycle is repeated.

The weevil is controlled to some extent by insecticides, however, it has been impossible to completely eliminate the pecan weevil whereby pecans harvested have the grubs or larvae therein. The grubs or larvae must be removed from the shelled pecans for successful marketing thereof. For purposes of this application, the grubs or larvae also will be referred to as worms.

Pecan processors have employed workers to hand pick the larvae or grubs out of the shelled pecans. When carried out on smaller broken pecan pieces, which are also processed for sale on the market, the hand picking process must be repeated a number of times in order to satisfactorily remove most of the worms. This is due to the fact that the larvae has a color which is about the same as the pecan meat and it is very difficult to distinguish the larvae from the meat of the broken pieces particularly since the size of the larvae is about the same as that of the broken pecan pieces. As can be understood each time the pecans are repicked, the processing cost increases.

Ultraviolet light has been used in the hand picking process and has been tried in sorting machines to enhance the detection and separation of the larvae. When illuminated or irradiated with ultraviolet light, the larvae fluoresces whereas the skins of the pecans do not fluoresce. This has improved the sorting or separating process, however, it still results in poor separation quality since the exposed meat of the broken pecan pieces also fluoresces when illuminated with ultraviolet light. Thus, even with ultraviolet light, it is difficult to distinguish the larvae from the pecan meat, both of which fluoresce under ultraviolet light. This results in many larvae being missed in the hand picking process and many pecan pieces being rejected along with the larvae in the sorting machines. In the hand picking process, even with ultraviolet light, the pecans must be repicked (thereby increasing the processing cost) to satisfactorily remove most of the worms.

SUMMARY OF THE INVENTION:

It is an object of the present invention to provide an improved method and system for processing shelled nuts for detecting worms or larvae in the nuts for separation and removal therefrom.

In carrying out the process, the shelled nuts are coated with an edible, non-fluorescent material and then irradiated to cause the worms to fluoresce to enhance detection. The detected worms then are separated from the nuts.

In one aspect, the nuts are irradiated or illuminated with a light of the type that will cause the worms to fluoresce. The edible, non-fluorescent material is water soluble and the nuts are coated with the material by applying to the nuts a solution comprising said material dissolved in water. The material is of the type that will prevent the nuts from fluorescing when the light is applied thereto. The material does not adhere to the worms and hence will not affect their fluorescense when the light is applied thereto. In addition, the color of the material is such that it does not significantly affect the appearance of the nuts when the nuts are coated with the material.

In the preferred embodiment, the process is carried out by soaking the nuts in a solution comprising said material dissolved in water to coat the nuts with said material. The nuts are removed from the solution and then dried. An ultraviolet light is applied to the coated nuts to cause the worms or larvae to fluoresce and enhance detection. The detected worms or larvae then are separated and removed from the nuts.

BACKGROUND:

In the processing of pecans, in one known processing facility, the pecans first are fed to a cracker which cracks the hulls of the pecans. The pecans then are fed to a sheller which pulls the hulls off of as many halves as possible. From the sheller the pecans fall to a separating system including separating screens which separate the halves from the broken pecan kernals and which also separates the broken pecan kernals including the broken hulls into four different sizes. The halves then are fed through a color sensitive sorting machine which separate the dark halves and remaining hulls from the lighter halves, the latter of which are dried and further separated from any remaining hulls and dark halves by workers or pickers. Float machines are employed to separate the meat from the hulls from each of the different sizes of the broken pecans. From the float machines, the sized, broken pecan pieces are dried and resized or sorted with screens into five different sizes or grades and placed in bins. The five sizes or grades are defined as large, medium, small, midget and granular. The larvae or worms of the pecan weevils in the pecans are sorted along with the pecan pieces into the pecan grades depending on their size. Generally the worms or larve will appear in the pecan pieces graded as medium, small, midget, and granular. The different grades of broken pecans are then separately fed to color sensitive sorting machines which separate the dark pecan pieces and hulls from the lighter pieces, the latter of which are placed in bins.

As indicated above, satisfactory separation of the worms or larvae from the broken pecan pieces by hand picking with natural or ultraviolet light is costly. The use of sorting machines employing ultraviolet light heretofore has not resulted in satisfactory separation since the machines reject too many pecans along with the larvae or worms.

In the processing of pecans, a successful coating material used is yellow in color which does not significantly affect the appearance of the pecans.

BRIEF DESCRIPTION OF THE DRAWINGS

FIG. 1 illustrates the sequence of processing pecans in one embodiment of the present invention;

FIG. 2 illustrates a sorting machine which may be employed to carry out the process of the present invention;

FIG. 3 is a breakaway perspective view of the machine of FIG. 2;

FIG. 4 illustrates the scanning head of the machine of FIGS. 2 and 3; and

FIG. 5 is an exploded view of one of the lens tubes of the scanning head of the sorting machine of FIG. 2.

DETAILED DESCRIPTION OF THE INVENTION

I have found that by coating the pecans with edible, non-fluorescent material, I can obtain vastily improved results in identifying and separating the larvae or worms form the pecans using ultraviolet light in either the hand picking process or in the sorting machines. From the standpoint of acceptability by the customer, the coating material should not significantly affect the appearance of the pecans. In a preferred embodiment, the coating material employed is a yellow food coloring. One such food color employed is egg-yellow food color (egg-yellow shade) distributed by Adams Extract of Austin, Texas. It is water soluble and its ingredients are U.S. Certified Food Color, water, and propylene glycol. In carrying out the process, 15 to 18 ounces of the food coloring are dissolved in 200 gallons of water. The solution is heated to 118°–122° F and the pecans (including the worms or larvae) soaked in the heated solution for about 4 minutes. The pecans then are removed from the solution, drained, and dried. In our operation, the coating process is carried out on the resized broken pecans, graded as medium, small and midget. Detection and separation of the worms or larvae from the coated pecans is carried out by applying an ultraviolet light to the coated pecans in the hand picking process and in the sorting machines. The yellow food coloring adheres and coats the pecans but does not adhere to or coat the worms. It appears that the larvae or worms have a wax like skin or a wax like film which in most cases repels the food coloring. Thus, the worms in the pecans fluoresce under ultraviolet light. The food coloring which coats the pecans does not fluoresce and prevents the pecan meat from fluoresing under ultraviolet light. It is believed that the food coloring blocks or prevents the ultraviolet light from penetrating or reaching the pecan meats and hence prevents fluorescense of the pecan meat. Thus, the worms or larvae are easily identified and separated from the coated pecans under the ultraviolet light. In the hand picking process using ultraviolet light, coating of the pecans with the yellow food coloring has greatly enhanced the number of worms that can be identified and separated from the pecans. In the sorting machines using ultraviolet light, coating of the pecans with yellow food coloring has greatly reduced the number of pecans rejected with the worms and has enabled the sorting machine using ultraviolet light to be an acceptable machine for worm-pecan separation purpose which machine previously was unacceptable.

Referring to FIG. 1, there will be described the present invention employed in the hand picking process. In this figure, there is illustrated a container 21 for holding the solution 23 of yellow food coloring dissolved in water. The solution is heated by gas burners illustrated at 24. A screen basket 25 having a fine mesh screen, is employed for holding the pecans to be processed. The pecans are identified in the basket at 27. They include the unwanted larvae or worms. The basket is adapted to be fitted into the container 21 to soak the pecans (and worms or larvae) in the heated solution for coating purpose. After the pecans are soaked for the desired time, the basket is removed and the excess solution is allowed to drain through the screen. After draining, the pecans are placed on another fine mesh screen 29 located over a heater and blower 31 for drying purpose. The pecans on screen 29 are also identified at 27. After the pecans are dried, they are placed in a hopper 33 located above one end of an endless conveyor 35 which is driven clockwise as shown in FIG. 1. The conveyor belt 35 is driven by a drive system illustrated at 37. Above the other end of the conveyor is located an ultraviolet light 39. At this end, there is a station 40 for an operator 41 or picker. Located below this end of the conveyor is a container 43 in which the separated pecans fall and a container 45 for holding the separated worms or larvae.

The hopper is operated by a power system illustrated at 47. The hopper feeds the coated pecans to the conveyor which moves the pecans (and worms or larva) under the ultraviolet light 39. The ultraviolet light causes the worms or larvae to fluoresce which are then detected and picked out and hence removed by the operator 41. The separated pecans fall in the container 43 while the operator deposits the worms or larvae in the container 45. By using the process of the present invention, in the hand picking process, a very large percentage of the worms are identified and removed in the first pass of the pecans under the ultraviolet light. Thus, the pecans are not required to be repicked, thereby resulting in a reduction in the processing cost.

In one embodiment the ultraviolet light is a 110 AC rated bulb produced by General Electric. It is identified as F40 blb blacklight. Another type of ultraviolet light that may be employed is a General Electric bulb identified as F15T8bl 15 watt blacklight. This bulb is used with a dark blue filter.

Referring now to FIGS. 2–4, there will be described a sorting machine which may be used to carry out the process of the present invention. This sorting machine is identified as a 5141-E color sorter available commercially from ICORE Acurex Corp. and described in their manual, revised June 25, 1973. The 5141-E color sorter uses three incandescent lights. Its original purpose was to discriminate and segregate particles which differ in color or contain visible blemishes or defects. It has been modified by replacing the three incandescent lights with three ultraviolet lights identified as Westinghouse 4W blacklight blue $F4T5b1b$. Other modifications will be described subsequently.

The sorting machine includes a feed system comprising a hopper 51 for holding the pecans (and worms or larvae to be separated); a vibrating feed tray 53 and counter rotating rollers 55 and 56 for aligning the pecans in single file. In FIG. 3, the pecans are identified at 27 while the worms or larvae to be separated are identified at 28. From the rollers, the pecans pass through a scanning head assembly 60 which comprises a housing 61 having an aperture 63 formed therethrough for the passage of the pecans. Also included are three photocell assemblies 64, 65 and 66; the three ultraviolet lights 67, 68 and 69 mentioned above; and three background plates 70, 71 and 72 located in the field of view of the photocell assemblies. Each photocell assembly contains a photomultiplier tube, lenses, slits and color filters which are collectively used to measure the amount of visible light radiated from fluorescense of the product as it passes through the scanning head.

The sorting machines also includes an electronic compartment 73 which contains signal circuits, the photocells, and its own signal circuitry. The signal circuits interpret the electrical current received from the photocells and accept or reject the product under observation. In the event of a reject, the reject impulse is delayed until the product has moved from the inspection position (aperture 63) to the rejection position. The rejection system is designed around an electrically operated air valve which is opened to allow a puff of air to deflect the defective or unwanted product from the free fall trajectory of accepted product. As shown in FIG. 3, the pecans (and worms or larvae) travel through the aperture 63 formed through the housing of the scanning head. The pecans from which the worms or larvae have been separated pass through a chute 75 where they fall to a collecting bin 77. If the photocell and electronic system senses fluorescense due to a worm or larvae, the air valve is opened to allow a puff of air to be injected through a conduit 79 located downstream of the housing 61 and at the junction of chute 75 with another chute 80. The system is timed such that the puff of air is delayed following sensing of fluorescense whereby the air will reject or deflect the worm or larvae sensed into the chute 80 where it will fall into a collecting bin 81. Thus, the accepted pecans pass through chute 75 and are collected in a bin 77 whereas the rejected worms or larvae pass through chute 80 and are collected in a bin 81. Located below the rollers 55 and 56 under the machine is another bin or container 83 which collects dust or debris which drop through the rollers and fall through a chute 85.

In carrying out the process using the sorting machine of FIGS. 2–4 the pecans (including the worms or larvae) are soaked in the heated solution comprising the egg-yellow food coloring dissolved in water as described above. A soaking system similar to the container 21, burners 24 and the basket 25 of FIG. 1 may be employed for soaking the pecans in the heated solution. The pecans then are drained, dried and placed in the hopper 51 for passage through the aperture 63 of the scanning head for detection by the photocell assemblies of the worms or larvae when they fluoresce when illuminated with ultraviolet light from the ultraviolet light bulbs 67, 68 and 69. The detected worms or larvae are separated from the pecans by the controlled air rejection system which comprises the air conduit 79.

ICORE produces and sells another sorting machine which is designed specifically for using ultraviolet light. The purpose of this machine is to discriminate and segregate particles that contain blemishes or defects that fluoresce under ultraviolet illumination. It is identified as Model No. 5141UV. It is similar to the 5141-E color sorter but includes six ultraviolet light bulbs (three pairs spaced 120° apart) for detecting fluorescence in the product to be rejected. As mentioned above, unless the pecans are coated in accordance with the present invention, this machine (Model No. 5141UV) is unacceptable to us for separating worms or larvae from pecans since it rejects to many pecans along with the worms. By coating the pecans in accordance with the present invention, however, the machine has proved to be very satisfactory in separating the worms or larvae from the pecans.

As mentioned above, the 5141-E color sorter has been modified for use in the process of the present invention for separating worms from pecans. The modification is to the scanning head. The three incandescent light bulbs have beem removed and three ultraviolet lights inserted in their place. Each ultraviolet light is a 4 watt, 110 volt AC bulb. The bulbs are wired in parallel and each bulb includes a starter. The bulbs are wired to a ballast transformer which is plugged into a 110 volt AC outlet. The reflector 89 was removed. The inside of the housing 61 and the cover 91 were painted charcoal black (they were white). The background plates 70, 71 and 72 were also painted black. The lens tubes 64A, 65A and 66A of the photocell assemblies were modified. Referring to FIG. 5 each lens tube comprises a forward lens tube 93 and a photocell lens tube 95. Located in the photocell lens tube 95 is a filter 97, a slit ring 99, having a slit 100 and a lens 101. Members 103 are retainers for ring 99 while member 105 is a spacer. Member 107 is an O-ring. Located in the forward lens tube 93 are lenses 109 and a disc 111 having an aperture 113. Member 115 is a glass window; member 117 is a lens nut; members 119 are O-rings and members 121 are spacers. In each lens tube, the filter 97 was removed and replaced with two filters. The slit ring 99 has been replaced with a slit ring having a wider slit. The width of the slit may vary from 0.125 to 0.175 of an inch. The disc 111 has also been removed. The disc originally employed had a diameter of 15/16 of an inch. Its aperture 113 was ⅛ of an inch in diameter. By removing the disc 111 much more light is allowed to pass to the photocell.

For use in carrying out the process of the present invention wherein the pecans are coated with a material to prevent the pecans from fluoresing as described above, the modified 5141-E color sorter has proved to be very satisfactory in separating worms or larvae from pecans. Since the three ultraviolet bulbs are wired in parallel, if one fails to operate, the other two will continue to operate. By coating the pecans in accordance with the present invention the modified 5141-E color sorter will satisfactorily distinguish and separate the worms whether it uses three or two ultraviolet light bulbs. With three ultraviolet bulbs, only two photocells are necessary. With two ultraviolet bulbs, only one photocell is necessary. Three ultraviolet bulbs are now employed since the machine as now set up employs instrumentation for three sensors (three photocell assemblies). By coating the pecans in accordance with the present invention only one ultraviolet light bulb (a larger bulb) and only one photocell assembly and signal circuit are needed to satisfactorily separate the worms or larvae from the pecans if the ultraviolet light bulb is properly mounted such that the light from the bulb shines directly on the pecans. This has advantages since it reduces the cost of the machine. In this embodiment the ultraviolet light bulb is mounted on the same side of the aperture 63 as the lens tube and photocell assembly such that the length of the bulb is perpendicular to the axis of the lens tube. The bulb employed may be a Westinghouse 6W blacklight blue bulb F6T5/b1b.

In the modified 5141-E color sorter, the three ultraviolet bulbs may be connected in series whereby if one of the bulbs fail to operate the other two will be prevented from operating. With the series connection there will be required only one starter for starting the three bulbs.

As mentioned above, the material for coating the pecans should have the following characteristics. It should not fluoresce when illuminated with ultraviolet light. It should be capable of coating the pecans but not adhering to the worms thereby allowing the worms to fluoresce under ultraviolet light but preventing the pecans from fluoresing. It should be edible and safe. It should be capable of being easily applied to the pecans. Preferably the material should be water soluble whereby it can be dissolved in water to allow the pecans to be coated with the material by soaking the pecans in the solution formed by dissolving the material in the water. It should also not significantly affect the appearance of the pecans.

The yellow food coloring mentioned above and distributed by Adams Extract meets the above requirements. Since it has a yellow color it does not affect the appearance of the pecans from the standpoint of color. Pecans processed in accordance with the present invention using the yellow food coloring has been accepted by out customers. In addition, the yellow food coloring is relatively inexpensive. It is believed that of the ingredients, the U.S. Certified Food Color prevents the pecans from fluorescing under ultraviolet light.

Food coloring produced by other companies also has been tested and found to be acceptable in carrying out the process of the present invention. For example, French's Yellow Food Coloring and McCormicks Yellow Food Coloring have been tested and found to be acceptable and useable in the process of the present invention. These food colors may be used in the same manner as that of Adams Extract for coating the pecans. In this respect, these food colors may be dissolved in water, the solution heated and the pecans (including the worms or larvae) soaked in the heated solution for coating the pecans. In using these food colors, 15 to 18 ounces thereof may be dissolved in 200 gallons of water and the solution heated to 118°–122° F. The pecans are soaked in the heated solution for about four minutes. Under ultraviolet light the pecan meats do not fluoresce however, the worms do fluoresce and are easily identified. The yellow food coloring of McCormicks and French's workers as well as the yellow food coloring of Adams Extract. It is believed that the food color in the yellow food coloring of Adams Extract, McCormicks and French's is yellow No. 5, which is of the AZO dye group, a synthetic dye made from coal. As is well known yellow No. 5 is a safe and edible food dye. In tests conducted, yellow No. 5 in powder form has been mixed with water and the pecans soaked in the solution and tested under ultraviolet light. The yellow No. 5 prevents the pecans from fluoresing but allows the worms to fluoresce whereby they may be easily identified. Thus, the food dye, yellow No. 5 may be used in carrying out the process of the present invention.

I have satisfactorily carried out the process of the present invention by soaking the pecans (for coating purposes) in unheated solutions formed by dissolving in tap water the yellow food coloring of each of the three Companies mentioned above and the yellow No. 5 dye. If an unheated solution is used, the pecans are satisfactorily coated if more yellow food coloring and yellow No. 5 dye is used than that used for a heated solution. The yellow food coloring of the three Companies mentioned above are more convenient to use and hence are preferred over the food dye yellow No. 5 in powder form.

The formula for the food yellow No. 5 color is as follows:

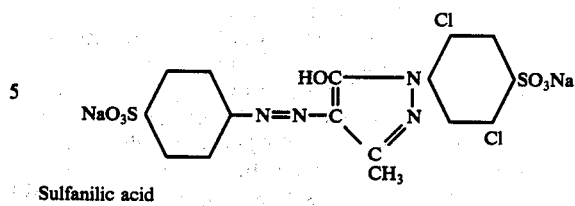

Sulfanilic acid

→1-(2,5-Dichloro-4-sulfophenyl)-3-methyl-5-pyrazolone

In addition to the above, other types of edible coloring or materials have been tried and found to work satisfactory. For example, I have tested the orange flavored drink "Tang" with satisfactory results. I have mixed 5 tablespoons of Tang in ½ cup of water making a strong solution. The solution was heated to nearly boiling and the pecans soaked in the solution for 5 minutes. The pecan meats were orange, nearly yellow. After drying, the pecans were illuminated with ultraviolet light. The pecan meat did not fluoresce, however, the worms did fluoresce under the ultraviolet light and were easily identified. I also mixed five tablespoons of Tang in ½ cup of tap water or cold water. The pecans were soaked in the solution with no heat applied thereto. The pecans were dried and placed under ultraviolet light. The pecans did not fluoresce, however, the worms did fluoresce and were easily identified. The Tang used in carrying out the tests has the following ingredients: sugar, citric acid (for tartness), calcium phosphates (regulate tartness and prevent caking), modified starches (provide body), potassium citrate (regulates tartness), cellulose gum (vegetable gum-provides body), natural orange flavor, vitamin C, hydrogenated coconut oil, artificial flavor, artificial color, vitamin A palmitate, BHA (A preservative). The Tang is manufactured by General Foods Corporation, White Plains, New York 10625, under U.S. Pat. Nos. 3,023,106 and 3,397,063. Although the Tang proved to be satisfactory in carrying out the process, it is much more expensive than the yellow food coloring or food dye yellow No. 5 as described above.

I also tested artifically flavored orange pop-bars sold under the trademark Kool-Pops and produced by General Foods Corporation. Each pop-bar comprises a liquid solution in a plastic package which is intended to be frozen prior to consumption. Twelve packages are sold in a box having a net weight of 13.5 fluid ounces. Using just the orange solution out of one plastic package, I heated the solution and left the pecans in the hot solution for about 5 minutes. The pecan meats turned yellow. After drying, the pecans were placed under ultraviolet light. The pecans did not fluoresce, however, the worms did fluoresce and were easily identified. In a cold water solution, the results were not as good under ultraviolet light.

The ingredients of the Kool-Pops are as follows: Water, corn syrup, citric acid (provides tartness), cellulose gum (vegetable gum-improves texture), sodium benzoate (a preservative), polysorbate 60 (emulsifier-for uniform dispersion of flavor), artificial and natural flavors, artificial color, and BHA (a preservative in orange and cherry only). 399 ml.

Although the orange pop bars proved to be satisfactory in carrying out the process of the present invention, they are more expensive than the yellow food coloring or food dye yellow No. 5 as described above.

Other edible dyes and materials having colors different from orange and yellow may be employed in carrying out the process, however, they are not preferred at the present time and under ordinary circumstances since they change the appearance of the pecans. These other edible dyes and materials, however, may be used in the process if for example, the pecans are to be used for special festive occasions. For example, I have tried red food coloring produced by McCormick's and by Adams Extract. The steps carried out were the same as that employed in using the yellow food coloring produced by Adams Extract. The red food coloring prevents the pecans from fluoresing under ultraviolet light but allows the worms to fluoresce. The pecans, however, turned a dark red. I have also placed beets in a blender to obtain their juices and soaked and pecans in the juice. After drying, the pecans turned red. The pecans, however, did not fluoresce under ultraviolet light whereas the worms did fluoresce and were easily identified.

I have tested imitation flavored grape Kool-Aid produced by General Foods Corporation. I added one cup of water to one 0.23 ounce package of Kool-Aid. The solution was heated to nearly a boiling point and the pecans left in the hot solution for five minutes. After drying, the pecan meats were dark looking, nearly black. Under ultraviolet light, the worms fluoresce, however, the pecan meats do not fluoresce. The ingredients of the Kool-Aid are: citric acid (provides tartness), sugar, monosodium phosphate (controls acidity), artificial flavor, vitamin C, artificial color, vitamin A. 6.5 G. The same process was repeated using an unheated solution. Under ultraviolet light, the worms fluoresce, however, the pecan meats did not fluoresce. I also tested imitation raspberry Kool-Aid produced by General Foods Corporation. I added ½ cup of water to one 0.23 ounce package of the Kool-Aid. The solution was heated to nearly a boiling point and the pecans left in the solution for five minutes. After drying, the pecan meats were red. Under ultraviolet light, the pecan meats did not fluoresce, however the worms did fluoresce. The ingredients of this Kool-Aid are: citric acid (provides tartness), monocalcium phosphate (controls acidity), Vitamin C, artificial color, artificial flavor, Vitamin A. I also used the same process in an unheated solution and obtained the same results. In addition, I have tested artificially flavored cherry pop-bars sold under the trademark Kool-Pops and produced by General Foods Corporation. Using just the solution out of the package, I heated the solution and left the pecans in the hot solution for nearly five minutes. The pecan meats turned red in the solution. After drying, the pecans were placed under ultraviolet light. Under ultraviolet light the pecan meats did not fluoresce, however, the worms did fluoresce. Except for the color and flavor the ingredients of this flavor of Kool-Pops is the same as that of the orange Kool-Pops. In carrying out the same steps using unheated tap water, the results were not as good under ultraviolet light.

As a further embodiment, the pecans may be soaked in water, removed from the water, and while the pecans are still wet, they may be placed under the ultraviolet light for enhancing the detection of the worms for separation from the pecans. It has been found that the water coating prevents the pecans from fluoresing although the fluorescense of the worms is not as good as that obtained if the pecans are coated with the yellow food coloring as described above. The use of water for blocking the fluorescense from the pecans has disadvantages in the sorting machine since the water causes the pecans to stick together and hance prevents their proper feeding through the machine. This problem, however, is not as great in the hand picking process. If a water coating is to be used for blocking the fluorescence from the pecans under ultraviolet light, the pecans must be processed promptly to prevent them from molding. After processing to remove the worms, the pecans must be promptly dried.

I have also tried out the process of the present invention on shelled walnuts in which the larvae of the pecan weevil, Curculio Caryae were added. In separate tests conducted, I dissolved in water yellow food coloring produced by McCormicks and by Adams Extract and heated the solutions to a nearly boiling point. I soaked broken walnut pieces (with the added larvae) in the heated solutions for 5 minutes. The walnuts were removed from the solutions, dried and placed under ultraviolet light. The worms did fluoresce, however, the walnut pieces did not fluoresce under ultraviolet light as they do without the food coloring. Slightly more food coloring was needed than that needed for the pecans, in order to obtain better results.

As one example, I processed through the 5141UV sorter, pecans which were uncoated and pecans which were coated using the process of the present invention. The pecans testes were broken pieces which were graded as small as defined above. I placed 50 worms in 3 pounds of the pecans. I placed 1½ ounces of yellow food coloring produced by Adams Extract in 20 gallons of water and heated the solution to about 118°–122° F. I soaked the pecans in the heated solution for about 2 minutes. After drying, I ran the coated pecans through the 5141UV (ultraviolet) sorting machine. The machine rejected approximately ¼ pound of the pecans and worms. Forty-four worms were found in the rejected product. I made a second run, however, in this run I only placed 44 worms in 3 pounds of the pecans. The machine rejected approximately ¼ of 1 pound of pecans and worms. Forty-four worms were found in the rejected product.

With the machine set up in the same manner, I placed 60 worms in 3 pounds of the pecans. The pecans were not coated with the yellow food coloring. The reject product was 1.5 pounds of pecans and worms. Fifty-seven worms were found in the rejected product. Although the machine rejected a large number of worms it also rejected at least half of the pecans. Thus, it can be seen that without coating the pecans in accordance with the present invention, the machine rejects too many pecans and hence does not do a good job in separating the worms from the pecans. By coating the pecans in accordance with the present invention, however, the machine rejects a large number of worms and only a small number of pecans. Thus, the coating process of the present invention has allowed the machine to be an acceptable machine for separating worms or larvae from pecans.

In our own operations we use the coating process of the present invention in hand picking operations employing ultraviolet light; in the 5141 ultraviolet sorter; and in the 5141-E sorter modified as described above using the three ultraviolet bulbs for detecting and separating worms or larvae from the pecan pieces. As mentioned above, in carrying out the process the pecans preferably are coated by soaking the pecans in a heated solution formed by dissolving in water the yellow food coloring of either of the aforementioned three Companies.

I claim:

1. A method of processing a mixture of shelled nuts and worms or larvae in order to detect said worms or larvae in said mixture for separation therefrom, said mixture containing broken pieces of said nuts, said method comprising the steps of:

coating said mixture with a solution containing a water soluble, edible, non-fluorescent material, said material being of the type that will adhere to said nuts but will not adhere to the worms or larvae to any significant extent and hence will not affect the fluorescense of said worms or larvae when ultraviolet light is applied thereto, drying said mixture, applying ultra-violet light to said mixture thereby causing said worms or larvae to fluoresce whereby said worms or larvae may be readily detected, and separating the detected worms or larvae from said nuts.

2. The method of claim 1 wherein: said material does not significantly affect the color of said nuts.

3. The process of claim 1 wherein: said material has a color similar to that of said nuts to be processed.

4. The process of claim 3 wherein:

said mixture is coated with said solution by soaking said mixture in said solution, said mixture is removed from said solution and then dried.

5. A method of processing a mixture of shelled pecans and worms or larvae in order to detect said worms or larvae in said mixture for separation therefrom, said mixture containing broken pieces of said pecans, said method comprising the steps of:

applying to said mixture, a solution containing a water soluble, edible, non-fluorescent material, said material being of the type that will adhere to said pecans but will not adhere to the worms or larvae to any significant extent and hence will not affect the fluorescense of said worms or larvae when ultra-violet light is applied thereto, drying said mixture, applying ultra-violet light to said mixture thereby causing said worms or larvae to fluoresce whereby said worms or larvae may readily detected, and separating the detected worms or larvae from said pecans.

6. The method of claim 5 wherein:

said material is yellow in color.

7. The method of claim 5 wherein:

said material comprises food coloring.

8. The method of claim 5 wherein:

said material has a color such that after said pecans have been processed, said pecans have generally their same original color.

9. The method of claim 6 wherein:

said material comprises yellow food coloring.

10. A method of processing a mixture of shelled pecans and worms or larvae in order to detect said worms or larvae in said mixture for separation therefrom, said mixture containing broken pieces of said pecans, said method comprising the steps of:

soaking said mixture in a solution containing a water soluble, edible, non-fluorescent material, said material being of the type that will adhere to said pecans but will not adhere to the worms or larvae, to any significant extent, and hence will not affect the fluorescense of said worms or larvae when ultra-violet light is applied thereto, removing said mixture from said solution, drying said mixture, applying ultra-violet light to said mixture thereby causing said worms or larvae to fluoresce whereby said worms or larvae may be readily detected, and separating the detected worms or larvae from said pecans.

11. The method of claim 10 wherein:

said material is yellow in color.

12. The method of claim 10 wherein:

said solution is heated to a temperature above room temperature while said mixture is soaked therein.

13. The method of claim 12 wherein:

said material is yellow in color.

14. The method of claim 13 wherein:

said material comprises yellow food coloring.

15. The method of claim 10 wherein: said material has a color such that after said pecans have been processed, said pecans have generally their same original color.

16. The method of claim 10 wherein:

said material comprises food coloring.

* * * * *